United States Patent [19]

Lundin et al.

[11] Patent Number: 5,132,211

[45] Date of Patent: Jul. 21, 1992

[54] GEL BODY AND A METHOD FOR BIOLOGICAL STERILIZATION CONTROL

[75] Inventors: Jan-Olof Lundin, Kode; Marianne Hedström, Göteborg; Ulf Rönner, Askim, all of Sweden

[73] Assignee: Diffchamb AB, Hisings Backa, Sweden

[21] Appl. No.: 566,391

[22] PCT Filed: Feb. 15, 1989

[86] PCT No.: PCT/SE89/00065

§ 371 Date: Aug. 17, 1990

§ 102(e) Date: Aug. 17, 1990

[87] PCT Pub. No.: WO89/07458

PCT Pub. Date: Aug. 24, 1989

[30] Foreign Application Priority Data

Feb. 17, 1988 [SE] Sweden .................... 8800545

[51] Int. Cl.$^5$ .................. C12Q 1/22; C12N 11/14; C12N 11/02
[52] U.S. Cl. ........................ 435/31; 435/176; 435/177; 435/180; 435/182
[58] Field of Search .................... 435/31-34, 435/174-180, 182

[56] References Cited

U.S. PATENT DOCUMENTS

| | | | |
|---|---|---|---|
| 2,931,757 | 4/1960 | Rdzok et al. | 435/31 |
| 3,585,112 | 7/1967 | Ernst | 435/31 |
| 4,291,122 | 9/1981 | Orelski | 435/31 |
| 4,393,136 | 7/1983 | Chettham | 435/178 |
| 4,450,233 | 5/1984 | Mimura et al. | 435/178 |
| 4,526,867 | 7/1985 | Chibata et al. | 435/178 |
| 4,791,061 | 12/1988 | Sumino et al. | 435/178 |
| 4,797,358 | 1/1989 | Motai et al. | 435/178 |
| 4,828,997 | 5/1989 | Yamaguchi et al. | 435/178 |

OTHER PUBLICATIONS

Davis et al.: Microbiology 3rd Ed. p. 709 (1980).

*Primary Examiner*—David L. Lacey
*Assistant Examiner*—William K. Y. Chan
*Attorney, Agent, or Firm*—Scully, Scott, Murphy & Presser

[57] ABSTRACT

The invention relates to a gel body of a delimited physical form preferably containing water and characterized in that it a) contains an encapsulated apathogenic micro-organism having a known and reproducible resistance; b) has a porous structure with the size of the pores defined, said structure preventing the encapsulated micro-organism from diffusing out but allows a nutrient solution adjusted to the micro-organism to diffuse in and metabolites produced to diffuse; c) is thermally stable in various sterilization, pasteurization or cooking processes; d) is mechanically stable when transported through the process equipment for sterilization, pasteurization or cooking; e) is surface sterile; and f) is transparent in order to allow observation of possible growth of the micro-organism when incubated in a nutrient solution. Also, the invention relates to a method for carrying out biological control of a sterilization, pasteurization, or cooking process, the method being characterized in that one or more gel bodies according to claim 1 are added to the product to be sterilized, that the product containing gel bodies is subjected to sterilization, pasteurization, cooking or other heat treatment, that the gel body or bodies are separated from the sterilized product after the sterilization has been completed, that the gel body or gel bodies are incubated in a nutrient solution, and that possible growth of micro-organisms is indicated.

10 Claims, No Drawings

GEL BODY AND A METHOD FOR BIOLOGICAL STERILIZATION CONTROL

The present invention relates to a product and a method for biological control of a process of the type of sterilization, pasteurization or cooking.

Heat treatment of various products by sterilization, pasteurization or cooking for killing various micro-organisms is applied within the food industry, breweries and dairies, public health service, sanitary and medical article industry, drug industry etc. In monitoring such heat treatment processes within the health service and medical article industry so called spore slips of paper are used. Such paper slips are caused to absorb various types of spores, for example, of *Bacillus subtilis* and of *Bacillus stearothermphilus*, which are temperature stable up to specific temperature ranges. These spore slips are then placed together with non-sterile sanitary articles for sterilization in an autoclave at the temperature of about 120° C. for about 20 minutes, alternatively in a gaseous atmosphere of ethylene oxide, formaldehyde or heated steam. The spore slips are checked with respect to possible surviving spores by the slips being put in a nutrient solution provided with a pH indicator (e.g. BTB-bromothymol blue). A change of colour of the nutrient solution after having been incubated for 1-3 days at 37° C., alternatively 55-60° C., will indicate that the autoclave treatment has been incomplete.

The use of the spore slips mentioned above is limited to applications where the risk of contaminating the products and the process equipment is not crucial to the continued function of the same. This means that said method cannot be accepted for sterility control in food production, particularly not for direct process control of e.g. liquid food products where the spores from the spore slips would be transferred directly to the product and infect the same.

The remaining present alternatives of various types of sterility control are, for example, to registrate continuously the temperature development in the process by controlling the temperature in autoclaves and other sterility reactors. The disadvantage of this procedure resides in the fact that it is only possible to measure at random at specified points of the equipment, not directly on each particle in, for example a liquid product or a product containing pieces.

The present invention relates to a product and a method for a biological sterility control directly in various processes of sterilization, pasteurization or cooking without any risk of contaminating the product to be sterilized and the process equipment. More particularly, according to one aspect of the invention it relates to a preferably water-containing gel body, having a discrete or delimited physical form, said body being characterized in that it a) contains an encapsulated apathogenic micro-organism having a known and reproducible resistance;

b) has a porous structure with the size of the pores defined, said structure preventing the encapsulated micro-organism from diffusing out but allowing a nutrient solution adjusted to the micro-organism to diffuse in and metabolites produced to diffuse out;

c) is thermally stable in various sterilization processes;

d) is mechanically stable when transported through the process equipment for sterilization, pasteurization or cooking;

e) is surface sterile; and f) is transparent in order to allow observation of possible growth of the micro-organism when incubated in a nutrient solution.

The invention also relates to a method of conducting a biological control of a sterilization, pasteurization or cooking process, the method being characterized by the steps that one or more gel bodies according to the invention are added to the product to be sterilized, that the product containing gel bodies is subjected to conventional sterilization, and that the gel body or bodies are separated from the sterilized product after completion of the sterilization process and incubated in a nutrient solution adjusted to the micro-organism, where possible growth of the micro-organism is indicated, for example, by a colour change of the nutrient solution.

The gel body according to the invention can consist of any suitable gel material having the properties defined under a) to f). For instance, the gel material can consist of polyacrylamide, calcium alginate, polyurethane, gelatine, agar or a combination thereof.

The gel body can consist of one single gel material, e.g. polyacrylamide, preferably, however, it comprises a core of a gel material, e.g. polyacrylamide or gelatine, covered by one or more layers of another gel material, e.g. calcium alginate, with the purpose of ensuring that the gel body be tightly sealed with respect to micro organisms within the temperature range contemplated, thus to avoid infection of the product to be sterilized.

Gels of polyacrylamide are mechanically strong, thermally stable, easy to handle, and they are completely transparent. They are produced by polymerization of monomeric acrylamide with a cross-linked co-polymer, N,N'-methylenebis-acrylamide (known as "bis") in the presence of free radicals, which are supplied by a chemical initiator, such as ammonium persulphate, or a photochemical initiator, such as riboflavin. The reaction is usually controlled by addition of TEMED (N,N,N',N'-tetramethylethylenediamine), which furnishes tertiary amines. The pore size of the gel can be varied by a suitable choice of total acrylamide concentration and the degree of cross-linking. The temperature at the polymerization is also important to the size of the pores.

The upper limit of the size of the pores is determined by the size of the micro-organisms which are encapsulated in the gel body, said limit being some tenth or tenths of a $\mu$m. The lower limit of the size of the pores is determined by the molecular size of a) the components of the nutrient solution which is to diffuse into the gel body at incubation, and b) of metabolites from the micro-organism which are to diffuse out into the nutrient solution.

The gel body can be dried or aqueous, i.a. depending on the physical condition of the product to be sterilized. When used for sterilization control of e.g. food stuff, a high percentage of water imparts to the gel heat transferring properties which are identical with those of most liquid and solid food products, for which reason the heat killing effect in the gel can be directly applied to the respective product. Suitable water-containing gels are polyacrylamide with a water content exceeding 50%, calcium alginate or gelatine having more than 90% water, and polyurethane gel likewise containing more than 90% water.

The gel body according to the invention should have a delimited physical form, adjusted to the product subject to sterilization control and to the process equipment, and it can have a diameter from some millimeter up to ten millimeters or so, for example, it could have the size of a pea.

The micro-organism encapsulated in the gel body should be a well defined, apathogenic micro-organism having a known and reproducible resistance, and it can be a spore or a bacterium, a mould or yeast fungus etc. The resistance is defined by a so called D-value (Decimal Reduction Value), that is, the time of action/temperature/dose which will give a 90% kill of the spores. For e.g. *Bacillus stearothermophilus* the D-value at 121° C. will be about 1,5 minutes and for e.g. *Bacillus subtilis* the D-value at 160° C. will be 5-10 minutes.

Suitable micro-organisms are *Bacillus subtilis*, for example Niger ATCC 9372 (ATCC=The American Type Culture Collection, USA) or SSI MK1 (SSI=initials of the Strain Stock of the State Serum Institute, Denmark) and *Bacillus stearothermophilus*, for example, ATCC 7953 or NIH 7953 (NIH=National Institute of Health Collection, USA). These organisms are preferably used in the form of spores.

An important feature of the gel body according to the invention is the fact that it has to be thermally stable in various sterilization processes, that is, it has to be thermally stable at the sterilization temperature concerned, e.g. up to 140° C. Furthermore, the mechanical strength of the gel body has to be such that it will endure transport through pumps, conduits, heat exchangers etc.

Furthermore, the gel body has to be surface sterile; surface sterilization of the gel body is preferably carried out by the body being treated with an aqueous solution of hydrogen peroxide or subject to gas sterilization by formaldehyde or ethylene oxide.

The gel body should also be transparent; transparency allows the result of the control to be swiftly and simply indicated thanks to the fact that, for example, a colour change at incubation can be readily observed and a possible microscopic checking of growth can be readily carried out.

The gel body according to the invention has preferably the form of a sphere having a diameter of 1-10 mm. An embodiment, particularly preferred, of a "gel ball" according to the invention includes an inner ball (a core) of e.g. polyacrylamide gel with spores of a micro-organism encapsulated therein, plus a surface sterile outer cover, e.g. of a calcium alginate gel or gelatine, such combination giving a particularly spore-tight and surface sterile gel ball. Such a gel ball can be produced as follows:

PRODUCTION OF A PREFERRED GEL BODY

1. Preparation of a Polyacrylamide Core.

Three stock solutions are made. 25-35 g acrylamide and 0.5-1.5 g N,N'-methylenebis-acrylamide (bis) are prepared with water to 100 ml (stock solution A). 75-125 mg ammonium persulphate is dissolved in 1 ml water (stock solution B) and 0.1 ml TEMED (N,N,N',N'-tetramethyl-ethylenediamine) is dissolved in 1 ml water, to which is also added varying amounts of spores, e.g. of *Bacillus subtilis* (stock solution C). By diluting 1-5 ml A to 15 ml and adding 20-100 µl B and 20-100 µl C a basic solution for polymerization is obtained, which contains about 2-8% acrylamide and 0.1-0.5% bis. In a particular embodiment, by diluting 2.5 ml A to 15 ml and adding 40 µl B and 60 µl C, a basic solution for polymerization is obtained, which contains about 5% acrylamide and 0.2% bis. Now, from this solution a polyacrylamide body is molded, which is allowed to cure at 0-50° C., preferably at 25-30° C. Thereafter, the body is allowed to dwell for 5-6 min in distilled water.

2. Application of a Calcium Alginate Layer

The polyacrylamide body is dipped into a calcium alginate solution containing more than 90% water, preferably more than 97% water, at room temperature. Thereafter, an alginate film is precipitated on the gel body of polyacrylamide by the body being immersed in a salt solution, e.g. calcium chloride in water, at a concentration of at least 1-3%. Precipitation occurs during 1-20 hours at room temperature. The gel body is thereafter kept in distilled water.

3. Surface sterilization of the Gel Body.

The surface of the gel body of polyacrylamide/calcium alginate is thereafter sterilized by the body being treated with a solution of e.g. hydrogen peroxide in a concentration of 1-35%, after which the gel is kept in distilled water.

The steps 2 and 3 above can be repeated one or more times in order that a tight and surface sterile gel ball be ensured.

In carrying out the method according to the invention the gel body or bodies are added to the product to be heat treated. Then sterilization, pasteurization or cooking takes place in a conventional manner by carrying out, in batches or continously, a pressure or temperature treatment, steam sterilization, hot air sterilization, formaline or ethylenoxide sterilization etc.

When treating e.g. meat broth or starch solution in batches in an autoclave, 10-100 gel bodies or gel balls are added per 1000 liters of the product after which the product is treated for about 20 minutes in autoclave at about 121° C. When sterilizing continuously, gel bodies are added at desired time intervals to the product subject to continuous sterilization, or they are added in connection with restarting of a cleaned process unit, after which the product is passed through a heating zone during 1-10 minutes at a temperature of up to 140° C.

After sterilization having been completed the gel bodies are separated in a suitable manner. This can be carried out by filtering, flotation, sedimenting or the like, depending on the density of the gel body and on the form and state of the sterilized product.

After separation of the gel bodies from the sterilized product each gel body is aseptically transferred to a tube with a nutrient solution suited to the micro-organism. One way of establishing a possible growth of the spores in the gel body is by means of a colour indicator, e.g. BTB-bromothylmol blue, component of the nutrient solution. Growth, and acid produced thereby, will result in a decrease of pH, which causes the colour of the indicator to change from blue via green to yellow. Reading takes place within 1-3 days; a preliminary reading could perhaps be made already after 10-15 hours. Thereby an answer is obtained more quickly in case the process has been incomplete, meaning, that the spores have not been killed.

The reason for this lack of effect can be attributed to a defect sterilizer or difficult sterilizing conditions. The problem has to be identified immediately so that the necessary measures can be taken.

A possible growth of the spores can also be established visually by a microscopic inspection of colonies of vegetative cells. This offers the possibility to read quantatively the killing of spores which the process has brought about.

The gel body and the method of sterilizing control according to the invention can be applied within various fields, for example, in the food industry and there particularly for sterility control of continuously processed liquid products, or products containing pieces, such as pea soup, meat broth, starch solution etc., Thanks to the fact that the gel body, which in this case contains water and has heat transferring properties almost identical with those of the product, is subjected to exactly the same sterilizing conditions as the product, a reliable and effective sterility control of the product is attained.

We claim:

1. A method for carrying out biological control of a sterilization process which comprises:
   (a) adding to a product to be sterilized one or more gel bodies consisting essentially of a gel and encapsulated spores of an apathogenic micro-organism having a known and reproducible resistance, defined by the time of action/temperature/dose which will give a 90% kill of the spores, and further wherein said gel of said gel body consists essentially of a core of a gel, selected from the group consisting of polyacrylamide, gelatine, agar, calcium alginate, polyurethane and combinations thereof, and one or more layers of a gel of calcium alginate or gelatine applied thereon, and further wherein the gel body has a porous structure, preventing the encapsulated spores from diffusing out but allowing a nutrient solution adjusted to the micro-organism to diffuse in and metabolites produced to diffuse out; is thermally and mechanically stable to sterilization, pasteurization and cooking; is surface sterile; and is transparent in order to allow observation of possible growth of the micro-organism when incubated in a nutrient solution;
   (b) exposing the product containing said one or more gel bodies to sterilizing conditions at elevated temperatures;
   (c) separating the gel body or bodies from the sterilized product, after sterilization has been completed, in an aseptic manner; and
   (d) incubating the gel body or bodies of step (c) in a nutrient solution in order to determine possible growth of the micro-organism.

2. A gel body having a delimited physical form wherein the gel body consists essentially of a gel and encapsulated spores of an apathogenic micro-organism having a known and reproducible resistance to heat, defined by the time of action/temperature/dose which will give a 90% kill of spores, and further wherein said gel of said gel body consists essentially of a core of a gel selected from the group consisting of polyacrylamide, gelatine, agar, calcium alginate, polyurethane and combinations thereof, and one or more layers of a gel of calcium alginate or gelatine applied thereon; and further wherein the gel body has a porous structure, preventing the encapsulated spores from diffusing out but allowing a nutrient solution adjusted to the micro-organism to diffuse in and metabolites produced to diffuse out; is thermally and mechanically stable to sterilization, pasteurization and cooking; is surface sterile; and is transparent in order to allow observation of possible growth of the micro-organism when incubated in a nutrient solution.

3. The gel body as in claim 2, wherein the encapsulated spores of an apathogenic micro-organism are temperature specific.

4. The gel body as in claim 3, wherein the temperature specific encapsulated spores of an apathogenic micro-organism are selected from the group consisting of *Bacillus subtilis* and *Bacillus stearothermophilus*.

5. The gel body as in claim 2, wherein the surface has been sterilized by treating the surface with hydrogen peroxide solution and then placing the gel body in distilled water.

6. A method for carrying out biological control of a sterilization process which comprises:
   (a) adding to a product to be sterilized one or more gel bodies consisting essentially of a gel and encapsulated spores of an apathogenic micro-organism having a known and reproducible resistance, defined by the time of action/temperature/dose which will give a 90% kill of the spores, and further wherein said gel of said gel body consists essentially of a core of a gel selected from the group consisting of polyacrylamide, gelatine, agar, calcium alginate, polyurethane and combinations thereof, and one or more layers of a gel of calcium alginate or gelatine applied thereon; and further wherein the gel body contains water; has a porous structure, preventing the encapsulated spores from diffusing out but allowing a nutrient solution adjusted to the micro-organism to diffuse in and metabolites produced to diffuse out; is thermally and mechanically stable to sterilization, pasteurization and cooking; is surface sterile; and is transparent in order to allow observation of possible growth of the micro-organism when incubated in a nutrient solution;
   (b) exposing the product containing said one or more gel bodies to sterilizing conditions at elevated temperatures;
   (c) separating the gel body or bodies from the sterilized product, after sterilization has been completed, in an aseptic manner; and
   (d) incubating the gel body or bodies of step (c) in a nutrient solution in order to determine possible growth of the micro-organism.

7. A gel body having a delimited physical form wherein the gel body consists essentially of a gel and encapsulated spores of an apathogenic micro-organism having a known and reproducible resistance to heat, defined by the time of action/temperature/dose which will give a 90% kill of spores, and further wherein said gel of said gel body consists essentially of a core of a gel selected from the group consisting of polyacrylamide, gelatine, agar, calcium alginate, polyurethane and combinations thereof, and one or more layers of a gel of calcium alginate or gelatine applied thereon; and further wherein the gel body contains water; has a porous structure, preventing the encapsulated spores from diffusing out but allowing a nutrient solution adjusted to the micro-organism to diffuse in and metabolites produced to diffuse out; is thermally and mechanically stable to sterilization, pasteurization and cooking; is surface sterile; and is transparent in order to allow observation of possible growth of the micro-organism when incubated in a nutrient solution.

8. The gel body as in claim 7, wherein the encapsulated spores of an apathogenic micro-organism are temperature specific.

9. The gel body as in claim 8, wherein the temperature specific encapsulated spores of an apathogenic micro-organism are selected from the group consisting of *Bacillus subtilis* and *Bacillus stearothermophilus*.

10. The gel body as in claim 7, wherein the surface has been sterilized by treating the surface with hydrogen peroxide solution and then placing the gel body in distilled water.

* * * * *